(12) United States Patent
Kino et al.

(10) Patent No.: US 7,939,294 B2
(45) Date of Patent: May 10, 2011

(54) DNA ENCODING PROTEINS HAVING DIPEPTIDE-SYNTHESIZING ACTIVITY AND METHODS OF USING THE SAME

(75) Inventors: Kuniki Kino, Chiba (JP); Youichi Kotanaka, Tokyo (JP); Makoto Yagasaki, Hofu (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 0 days.

(21) Appl. No.: 12/442,472

(22) PCT Filed: Sep. 25, 2007

(86) PCT No.: PCT/JP2007/068509
§ 371 (c)(1),
(2), (4) Date: Mar. 23, 2009

(87) PCT Pub. No.: WO2008/038613
PCT Pub. Date: Mar. 4, 2008

(65) Prior Publication Data
US 2010/0129866 A1    May 27, 2010

(30) Foreign Application Priority Data
Sep. 25, 2006    (JP) ................................ 2006-258278

(51) Int. Cl.
*C12P 21/06* (2006.01)
(52) U.S. Cl. ........ 435/69.1; 435/6; 435/320.1; 435/252; 435/325; 530/350
(58) Field of Classification Search .................. None
See application file for complete search history.

(56) References Cited

U.S. PATENT DOCUMENTS

| 5,095,139 A | 3/1992 | Loeffler et al. |
| 2004/0171106 A1 | 9/2004 | Hashimoto et al. |

FOREIGN PATENT DOCUMENTS

| JP | 1988(63)-101398 A | 5/1988 |
| WO | WO-2004/058960 A1 | 7/2004 |

OTHER PUBLICATIONS

Wells, Biochemistry, vol. 29, pp. 8509-8517, 1990.*
Seffernick et al. (J. Bacteriology, vol. 183, pp. 2405-2410, 2001).*
"Kokuritsu Dipeptid Kogyo Seiho no Kaihatsu", Yagasaki et al., Bio Industry, Sep. 12, 2006, Vol. 23, No. 9, pp. 26-34.
"Rhizocticin A, an antifungal phosphono-oligopeptide of *Bacillus subtilis* ATCC 6633: biological properties", by Kugler et al., Arch Microbiol, 1990, vol. 153, No. 3 pp. 276-281.
"Amino Acid Renketsu Koso no Tansaku to Dipeptid Gosei eno Riyo", Kino et al., Bio Industry, Sep. 12, 2006, vol. 23, No. 9, pp. 59-67.
"Ralstonia Solanacearum Yurai no Shinki L-Amino Acid Ligase o Mochiita L-Amino Acid Peptide Gosei", Nakazawa et al., Koso Kogaku Kenkyukai Dai 56 Kai Koenkai Koen Yoshishu Nov. 28, 2006, p. 51.
Tabata et al. "ywfE in *Bacillus subtilis* Codes for a Novel Enzyme, L-Amino Acid Ligase", J. Bacteriol., vol. 187, No. 15 (2005) 5195-202.
Kino et al., "A Novel L-Amino Acid Ligase from *Bacillus subtilis* NBRC3134, a Microorganism Producing Peptide-Antibiotic Rhizocticin", Biosci. Biotechnol. Biochem., vol. 73, No. 4 (2009) 901-7.
A. Yazgan et al., Bacilysin biosynthesis by a partially-purified enzyme fraction from *Bacillus subtilis*, Enzyme and Microbial Technology, 2001, No. 29, pp. 400-406.
M. Sakajoh et al., Cell-free synthesis of the dipeptide antibiotic bacilysin, Journal of Industrial Microbiology, 1987, No. 2, pp. 201-208.

* cited by examiner

*Primary Examiner* — Hope A Robinson
(74) *Attorney, Agent, or Firm* — Fitzpatrick, Cella, Harper & Scinto

(57) ABSTRACT

The present invention provides a protein having dipeptide-synthesizing activity, a DNA encoding the protein, a recombinant DNA containing the DNA, a transformant obtained via transformation with the recombinant DNA, a process for producing a protein having dipeptide-synthesizing activity using the transformant, a process for producing a dipeptide using a protein having dipeptide-synthesizing activity, and a process for producing a dipeptide using a culture or the like of a transformant or a microorganism that produces a protein having dipeptide-synthesizing activity as an enzyme source.

11 Claims, 1 Drawing Sheet

DNA ENCODING PROTEINS HAVING DIPEPTIDE-SYNTHESIZING ACTIVITY AND METHODS OF USING THE SAME

CROSS-REFERENCE TO PRIOR APPLICATION

This is the U.S. National Phase Application under 35 U.S.C. §371 of International Patent Application No. PCT/JP2007/068509 filed Sep. 25, 2007, which claims the benefit of Japanese Patent Application No. 2006-258278 filed Sep. 25, 2006, both of which are incorporated by reference herein. The International Application was published in Japanese on Apr. 3, 2008 as WO2008/038613 A1 under PCT Article 21 (2).

TECHNICAL FIELD

The present invention relates to a protein having dipeptide-synthesizing activity, a DNA encoding the protein, a recombinant DNA containing the DNA, a transformant obtained via transformation with the recombinant DNA, a process for producing a protein having dipeptide-synthesizing activity, a process for producing a dipeptide using a protein having dipeptide-synthesizing activity, and a process for producing a dipeptide using a microorganism or a transformant that produces a protein having dipeptide-synthesizing activity.

BACKGROUND ART

There is only basilicin synthetase that is known to produce dipeptide by peptide bond forming activity at an α-carboxyl group of L-amino acid, which is a synthetic enzyme of a dipeptide antibiotic derived from a microorganism belonging to the genus *Bacillus*. Basilicin synthetase is known to have activity of synthesizing basilicin (L-alanyl-L-anticapsin, L-Ala-L-anticapsin) and L-alanyl-L-alanine (L-Ala-L-Ala) (see J. Ind. Microbiol., 2, 201-208 (1987) and Enzyme. Microbial. Technol., 29, 400-406 (2001)). It has been recently reported that this enzyme has activity of forming various dipeptides from the same or different free amino acids in various combinations (see WO 2004/058960).

However, the productive efficiency of some dipeptides is insufficient because of the substrate specificity of the above enzyme. Hence, a new dipeptide synthetase having substrate specificity differing from that of the above enzyme is required.

*Bacillus subtilis* ATCC6633 ("ATCC" is the American Type Culture Collection) is known to produce peptide antimicrobials, rhizocticin A (L-Arg-L-2-amino-5-phosphono-3-cis-pentenoic acid, L-Arg-L-APPA), rhizocticin B (L-Val-L-Arg-L-APPA), rhizocticin C (L-Ile-L-Arg-L-APPA), and rhizocticin D (L-Leu-L-Arg-L-APPA) (see Arch. Micromiol., 153, 276-281 (1990)). However, the biosynthetic pathway thereof, proteins involved in the biosynthesis thereof, and genes involved in the biosynthesis thereof remain unknown.

DISCLOSURE OF THE INVENTION

Object to be Attained by the Invention

An object of the present invention is to provide a protein having dipeptide-synthesizing activity, a DNA encoding the protein, a recombinant DNA containing the DNA, a transformant obtained via transformation with the recombinant DNA, a process for producing a protein having dipeptide-synthesizing activity using the transformant or the like, a process for producing a dipeptide using the protein having dipeptide-synthesizing activity, and a process for producing a dipeptide using a culture or the like of a transformant or a microorganism that produces the protein having dipeptide-synthesizing activity as an enzyme source.

Means for Attaining the Object

The present invention relates to the following (1) to (10).
(1) A protein according to any one of the following [1] to [3]:
 [1] a protein having the amino acid sequence shown by SEQ ID NO: 1;
 [2] a protein consisting of an amino acid sequence that has a deletion, a substitution, or an addition of one or more amino acids in the amino acid sequence shown by SEQ ID NO: 1, and having dipeptide-synthesizing activity; and
 [3] a protein consisting of an amino acid sequence that has 80% or more homology with the amino acid sequence shown by SEQ ID NO: 1, and having dipeptide-synthesizing activity.
(2) A DNA according to any one of the following [1] to [3]:
 [1] a DNA encoding the protein of (1) above;
 [2] a DNA having the nucleotide sequence shown by SEQ ID NO: 2; and
 [3] a DNA hybridizing under stringent conditions to a DNA consisting of a nucleotide sequence complementary to the nucleotide sequence shown by SEQ ID NO: 2, and encoding a protein having dipeptide-synthesizing activity.
(3) A recombinant DNA containing the DNA of (2) above.
(4) A transformant having the recombinant DNA of (3) above.
(5) The transformant of (4) above, wherein the transformant is obtained using a microorganism as a host.
(6) The transformant of (5) above, wherein the microorganism belongs to the genus *Escherichia*.
(7) A process for producing the protein of (1) above, comprising culturing a microorganism capable of producing the protein of (1) above in a medium, forming and accumulating the protein in a culture, and recovering the protein from the culture.
(8) The process of (7) above, wherein the microorganism capable of producing the protein of (1) above is the transformant according to any one of (4) to (6).
(9) A process for producing a dipeptide, comprising allowing a culture or a treated culture of a microorganism capable of producing the protein of (1) above or the protein of (1) above, and one or more kinds of amino acid to be present in an aqueous medium, forming and accumulating the dipeptide in the medium, and then recovering the dipeptide from the medium.
(10) The process of (9) above, wherein the microorganism capable of producing the protein of (1) above is the transformant according to any one of (4) to (6) above.

Effects of the Invention

According to the present invention, a protein having dipeptide-synthesizing activity can be produced. Furthermore, a dipeptide can be produced using the protein or a transformant or a microorganism capable of producing the protein.

3

EXPLANATION OF SYMBOLS

Figure 1:
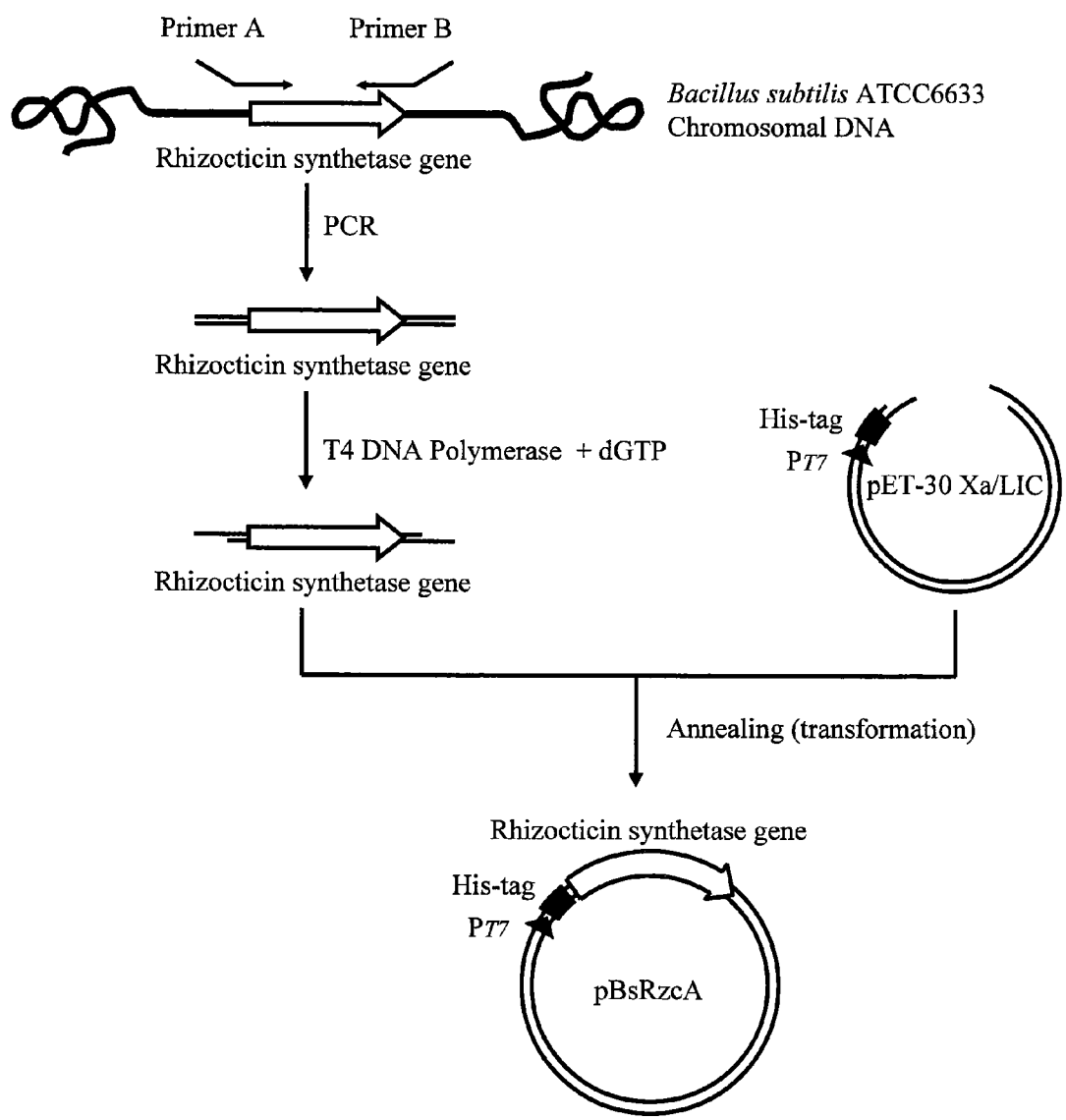
FIG. 1 shows a process for construction of plasmid pBsRzcA.

In FIG. 1, "PT7" denotes T7 promoter gene and "His-tag" denotes a histidine tag (His-tag) sequence.

BEST MODES FOR CARRYING OUT THE INVENTION

1. Protein of the Present Invention

Examples of the protein of the present invention include:
[1] a protein having the amino acid sequence shown by SEQ ID NO: 1;
[2] a protein consisting of an amino acid sequence that has a deletion, a substitution, or an addition of one or more amino acids in the amino acid sequence shown by SEQ ID NO: 1, and having dipeptide-synthesizing activity; and
[3] a protein consisting of an amino acid sequence that has 80% or more homology with the amino acid sequence shown by SEQ ID NO: 1, and having dipeptide-synthesizing activity.

The above protein consisting of an amino acid sequence that has a deletion, a substitution, or an addition of one or more amino acids and having dipeptide-synthesizing activity can be obtained by site-directed mutagenesis according to Molecular Cloning, A Laboratory Manual, 2$^{nd}$ Edition Cold Spring Harbor Laboratory Press (1989) (hereinafter, abbreviated as Molecular Cloning, 2$^{nd}$ Edition), Current Protocols in Molecular Biology, John Wiley & Sons (1987-1997) (hereinafter, abbreviated as Current Protocols In Molecular Biology), Nucleic Acids Research, 10, 6487 (1982), Proc. Natl. Acad. Sci. U.S.A., 79, 6409 (1982), Gene, 34, 315 (1985), Nucleic Acids Research, 13, 4431 (1985), Proc. Natl. Acad. Sci. U.S.A., 82, 488 (1985), or the like. For example, the protein can be obtained by introducing site-specific mutation into a DNA encoding a protein comprising the amino acid sequence shown by SEQ ID NO: 1.

The number of amino acids to be deleted, substituted, or added is not particularly limited, but is the number such that deletion, substitution, or addition can be carried out by a known method such as the above site-specific mutagenesis. The number of amino acids is 1 to dozens of, preferably 1 to 20, more preferably 1 to 10, and further more preferably 1 to 5.

The phrase "a deletion, a substitution, or an addition of one or more amino acids in the amino acid sequence shown by SEQ ID NO: 1" means that, at any position in such sequence, 1 or a plurality of amino acids may be deleted, substituted, or added.

Moreover, examples of amino acid positions in which amino acid deletion, substitution, or addition can be introduced, include one to several amino acid positions on the N-terminal side and the C-terminal side of the amino acid sequence shown by SEQ ID NO: 1.

A deletion, a substitution, and an addition may be introduced simultaneously. Amino acids to be substituted or added may be natural or unnatural. Examples of natural amino acids include L-alanine, L-asparagine, L-aspartic acid, L-arginine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, and L-cysteine.

Examples of amino acids that are mutually substitutable are listed below. Amino acids in the same group can be substituted with each other.

4

Group A: leucine, isoleucine, norleucine, valine, norvaline, alanine, 2-aminobutanoic acid, methionine, O-methylserine, t-butylglycine, t-butylalanine, and cyclohexylalanine
Group B: aspartic acid, glutamic acid, isoaspartic acid, isoglutamic acid, 2-aminoadipic acid, and 2-aminosuberic acid
Group C: asparagine and glutamine
Group D: lysine, arginine, ornithine, 2,4-diaminobutanoic acid, and 2,3-diaminopropionic acid
Group E: proline, 3-hydroxyproline, and 4-hydroxyproline
Group F: serine, threonine, and homoserine
Group G: phenylalanine and tyrosine Furthermore, the protein of the present invention desirably has 80% or more, preferably 90% or more, more preferably 94% or more, further more preferably 98% or more, and particularly preferably 99% or more homology with the amino acid sequence shown by SEQ ID NO: 1 so that the protein has dipeptide-synthesizing activity.

Amino acid sequence homology or nucleotide sequence homology can be determined using the algorithm BLAST (Basic Local Alignment Search Tool) of Karlin and Altschul [Pro. Natl. Acad. Sci. U.S.A., 90, 5873 (1993)] or FASTA DNA and protein sequence alignment protocol [Methods Enzymol., 183, 63 (1990)]. Based on the algorithm BLAST, a program called BLASTN or BLASTX has been developed [J. Mol. Biol., 215, 403 (1990)]. When nucleotide sequences are analyzed by BLASTN based on BLAST, parameters such as Score=100 and word length=12 are employed. Also, when amino acid sequences are analyzed by BLASTX based on BLAST, parameters such as score=50 and word length=3 are employed. When BLAST and Gapped BLAST program are employed, default parameters of each program are used. Specific techniques for these analytical methods are known.

Furthermore, a protein consisting of an amino acid sequence having 80% or more, preferably 90% or more, more preferably 94% or more, further more preferably 98% or more, and particularly preferably 99% or more homology with the amino acid sequence shown by SEQ ID NO: 1, and having dipeptide-synthesizing activity is also the protein of the present invention. Amino acid sequence homology can be determined using BLAST and FASTA as described above.

An example of a method for confirming that the protein of the present invention is a protein having dipeptide-synthesizing activity involves preparing a transformant that expresses the protein of the present invention by a DNA recombination method, producing the protein of the present invention using the transformant, allowing the protein of the present invention, one or more kinds of amino acid, preferably two kinds of amino acid selected from among L-amino acid and glycine, and ATP to be present in an aqueous medium, and then analyzing by HPLC or the like whether or not a dipeptide is formed and accumulated in the aqueous medium.

2. DNA of the Present Invention

Examples of the DNA of the present invention include:
[1] a DNA encoding the protein of the present invention according to any one of [1] to [3] in 1 above;
[2] a DNA having the nucleotide sequence shown by SEQ ID NO: 2; and
[3] a DNA hybridizing under stringent conditions to a DNA consisting of a nucleotide sequence complementary to the nucleotide sequence shown by SEQ ID NO: 2, and encoding a protein having dipeptide-synthesizing activity.

Here the term "hybridizing" refers to a step such that a DNA hybridizes to a DNA having a specific nucleotide sequence or a part of the DNA. Therefore, the DNA having a specific nucleotide sequence or a nucleotide sequence of a part of the DNA is useful as a probe for Northern or Southern blot analysis or may be a DNA with a length such that the DNA can be used as an oligonucleotide primer for polymerase chain reaction (PCR) analysis. An example of a DNA to be used as a probe for Northern or Southern blot analysis is a DNA with a length of at least 100 nucleotides or more, preferably 200 nucleotides or more, and more preferably 500 nucleotides or more. An example of a DNA to be used as an oligonucleotide primer is a DNA with a length of at least 10 nucleotides or more and preferably 15 nucleotides or more.

Experimental methods for DNA hybridization are known well. For example, hybridization conditions are determined according to Molecular Cloning $2^{nd}$ Edition, $3^{rd}$ Edition (2001), Methods for General and Molecular Bacteriology, ASM Press (1994), and Immunology methods manual, Academic press (Molecular) in addition to many other standard textbooks and then an experiment can be conducted.

The above stringent conditions are, for example, conditions under which a DNA-immobilized filter and a probe DNA are incubated overnight at 42° C. in a solution containing 50% formamide, 5×SSC (750 mM sodium chloride, 75 mM sodium citrate), 50 mM sodium phosphate (pH 7.6), 5×Denhardt's solution, 10% dextran sulfate, and denatured 20 μg/L salmon sperm DNA, following which the filter is washed in a 0.2×SSC solution at approximately 65° C., for example. Less stringent conditions can also be employed herein. Stringent conditions can be varied via adjustment of formamide concentration (the lower the formamide concentration, the less the stringency), change of salt concentration, and change of temperature conditions. Such less stringent conditions are, for example, conditions under which incubation is carried out overnight at 37° C. in a solution containing 6×SSCE (20×SSCE: 3 mol/L sodium chloride, 0.2 mol/L sodium dihydrogenphosphate, 0.02 mol/L EDTA, and pH 7.4), 0.5% SDS, 30% formamide, and denatured 100 μg/L salmon sperm DNA, followed by washing using 1×SSC and 0.1% SDS solutions at 50° C. Even less stringent conditions are, for example, the above less stringent conditions under which hybridization is carried out using a solution with a high salt concentration (e.g., 5×SSC), followed by washing.

Various conditions described above can also be set by adding or changing a blocking reagent to be used to suppress the background conditions of a hybridization experiment. Such addition of a blocking reagent may be associated with changes in hybridization conditions, and may thus be used to adjust the conditions.

An example of a DNA that can hybridize under the above-mentioned stringent conditions is a DNA having at least 80% or more, preferably 90% or more, more preferably 94% or more, further more preferably 98% or more, and particularly preferably 99% or more homology with the nucleotide sequence of the DNA of any one of [1] to [3] above, when calculation is performed based on the above parameters using the above program such as BLAST or FASTA.

Nucleotide sequence homology can be determined using the above-mentioned program such as BLAST or FASTA.

That a DNA hybridizing to the above DNA under stringent conditions is a DNA encoding a protein having dipeptide-synthesizing activity can be confirmed by a method that involves preparing a recombinant DNA that expresses the DNA, purifying the relevant protein from a culture that is obtained by culturing a microorganism (the microorganism is obtained by introducing the recombinant DNA into host cells), and then allowing the purified protein to be used as an enzyme source, and one or more kinds of amino acid and preferably two kinds of amino acid selected from among L-amino acid and glycine to be present in an aqueous medium, and then analyzing by HPLC or the like whether or not a dipeptide is formed and accumulated in the aqueous medium.

3. Microorganisms And Transformants To Be Used For the Process of the Present Invention Microorganisms and transformants to be used for the process of the present invention are not particularly limited as long as they are microorganisms and transformants capable of producing the protein of the present invention. Examples of such microorganisms include preferably microorganisms belonging to the genus *Bacillus*, preferably microorganisms belonging to *Bacillus subtilis*, and more preferably *Bacillus subtilis* ATCC6633. Examples of such transformant include transformants obtained via transformation with a DNA encoding the protein of the present invention.

Examples of transformants obtained via transformation with a DNA encoding the protein of the present invention include transformants obtained via transformation of host cells with a recombinant DNA containing the DNA in 2 above according to a known method. Examples of host cells include prokaryotes such as bacteria, yeast, animal cells, insect cells, and plant cells, preferably prokaryotes such as bacteria, and more preferably microorganisms belonging to the genus *Escherichia*.

4. Preparation of the DNA of the Present Invention

The DNA of the present invention can be obtained by carrying out Southern hybridization for a chromosomal DNA library of a microorganism belonging to the genus *Bacillus*, preferably a microorganism belonging to *Bacillus subtilis*, and more preferably *Bacillus subtilis* ATCC6633 using a probe that can be designed based on the nucleotide sequence shown by SEQ ID NO: 2, for example. Alternatively, the DNA can be obtained by carrying out PCR [PCR Protocols, Academic Press (1990)] using primer DNAs that can be designed based on the nucleotide sequence shown by SEQ ID NO: 2 and a chromosomal DNA of a microorganism, preferably a microorganism belonging to the genus *Bacillus*, more preferably a microorganism belonging to *Bacillus subtilis*, and further more preferably *Bacillus subtilis* ATCC6633 as a template.

Moreover, various gene sequence databases are searched for a sequence having 85% or more, preferably 90% or more, more preferably 95% or more, further more preferably 98% or more, and particularly preferably 99% or more homology with the nucleotide sequence of a DNA encoding the amino acid sequence shown by SEQ ID NO: 1. Based on the nucleotide sequence obtained by the search, the DNA of the present invention or a DNA to be used in the process of the present invention can also be obtained by the above-mentioned method from chromosomal DNAs, cDNA libraries, and the like of organisms having the nucleotide sequence.

The nucleotide sequence of the thus obtained DNA can be determined by directly incorporating the DNA into or digesting the DNA with an appropriate restriction enzyme or the like and then incorporating into a vector by a conventional method, introducing the thus obtained recombinant DNA into host cells, and then analyzing the resultant using a generally employed nucleotide sequence analysis method, such as a dideoxy chain termination method [Proc. Natl. Acad. Sci., U.S.A., 74, 5463 (1977)] or a nucleotide sequence analyzer such as an ABI3700 DNA analyzer (Applied Biosystems).

When the thus obtained DNA is a partial-length DNA as revealed by determination of the nucleotide sequence, the full-length DNA can be obtained by carrying out Southern hybridization or the like for a chromosomal DNA library using the partial-length DNA as a probe.

Moreover, based on the thus determined nucleotide sequence of the DNA, a target DNA can also be prepared by chemical synthesis using a Model 8905 DNA Synthesizer (Perseptive Biosystems) or the like.

An example of a DNA obtained as described above is a DNA having the nucleotide sequence shown by SEQ ID NO: 2.

Examples of a vector into which the DNA of the present invention is incorporated include pBluescriptII® KS(+) (Stratagene), pDIRECT [Nucleic Acids Res., 18, 6069 (1990)], pCR-Script Amp SK(+) (Stratagene), pT7Blue (Novagen), pCR II (Invitrogen Corporation), and pCR-TRAP® (GeneHunter).

Examples of host cells include microorganisms belonging to the genus *Escherichia*. Examples of such microorganisms belonging to the genus *Escherichia* include *Escherichia coli* XL1-Blue, *Escherichia coli* XL2-Blue® (Stratagene), *Escherichia coli* DH1, *Escherichia coli* MC1000, *Escherichia coli* ATCC 12435, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Escherichia coli* BL21, and *Escherichia coli* ME8415.

Any method can be used as a method for introducing a recombinant DNA, as long as it is a method for introducing a DNA into the above host cells. Examples of such method include a method using calcium ions [Proc. Natl. Acad. Sci., U.S.A., 69, 2110 (1972)], a protoplast method (JP Patent Publication (Kokai) No. 63-248394 (1988)), and electroporation [Nucleic Acids Res., 16, 6127 (1988)].

An example of the transformant of the present invention obtained by the above method is *Escherichia coli* Rosetta (DE3)/pBsRzcA that is a microorganism possessing a recombinant DNA containing a DNA having the nucleotide sequence shown by SEQ ID NO: 2.

5. Process for Producing Transformants and Microorganisms to be Used for the Processes of the Present Invention Based on the DNA of the present invention, a DNA fragment with an appropriate length containing a portion that encodes the protein of the present invention is prepared, as necessary. Also, the nucleotide sequence of a part that encodes the protein is subjected to nucleotide substitution so as to prepare an optimum codon for expression in a host. As a result, a transformant with an improved productivity of the protein can be obtained.

A recombinant DNA is prepared by inserting the DNA fragment downstream of a promoter of an appropriate expression vector.

The thus prepared recombinant DNA is introduced into host cells appropriate for the expression vector, so that a transformant that produces the protein of the present invention can be obtained.

Any host cells can be used, as long as they can express a target gene, such as prokaryotes (e.g., bacteria), yeast, animal cells, insect cells, and plant cells.

Expression vectors to be used herein can autonomously replicate within the host cells or can be incorporated into a chromosome and contains a promoter at a position into which the DNA of the present invention can be transcribed.

When a prokaryote such as a bacterium is used as a host cell, a recombinant DNA having the DNA of the present invention is preferably autonomously replicable in a prokaryote, and containing a promoter, a ribosome binding sequence, the DNA of the present invention, and a transcription termination sequence. A gene controlling a promoter may also be contained.

Examples of expression vectors include pBTrp2, pBTac1, pBTac2, pHelix1 (all of them are manufactured by Roche Diagnostics K.K.), pKK233-2 (Amersham•Pharmacia•Biotech), pSE280 (Invitrogen Corporation), pGEMEX-1® (Promega), pQE-8 (QIAGEN), pET-3 (Novagen), pKYP10 (JP Patent Publication (Kokai) No. 58-110600A (1983)), pKYP200 [Agric. Biol. Chem., 48, 669 (1984)], pLSA1 [Agric. Biol. Chem., 53, 277 (1989)], pGEL1 [Proc. Natl. Acad. Sci., U.S.A., 82, 4306 (1985)], BluescriptII® SK(+), pBluescript II® KS(−) (Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [Gene, 33, 103 (1985)], pSTV28 (Takara Bio Inc.), pUC118 (Takara Bio Inc.), and pPA1 (JP Patent Publication (Kokai) No. 63-233798 A (1988)).

As a promoter, any promoter may be used herein, as long as it functions within host cells such as *Escherichia coli*. Examples of such promoter include promoters derived from *Escherichia coli* or a phage, such as a trp promoter ($P_{trp}$), a lac promoter ($P_{lac}$), a $P_L$ promoter, a $P_R$ promoter, and a $P_{SE}$ promoter, an SPO1 promoter, an SPO2 promoter, and a penP promoter. Furthermore, artificially designed and altered promoters and the like can also be used herein, such as promoters in which two $P_{trp}$ are arranged in series, a tac promoter, a lacT7 promoter, and a let I promoter.

Moreover, an xylA promoter [Appl. Microbiol. Biotechnol., 35, 594-599 (1991)] to be expressed in a microorganism belonging to the genus *Bacillus*, a P54-6 promoter [Appl. Microbiol. Biotechnol., 53, 674-679 (2000)] to be expressed in a microorganism belonging to the genus *Corynebacterium*, or the like can also be used.

Furthermore, a plasmid, in which the distance between Shine-Dalgarno sequence that is a ribosome binding sequence and the initiation codon is appropriately regulated (e.g., 6 to 18 nucleotides) is preferably used.

In a recombinant DNA in which the DNA of the present invention is ligated to an expression vector, a transcription termination sequence is not always required, but a transcription termination sequence is preferably arranged immediately following a structural gene.

An example of such recombinant DNA is pBsRzcA.

Examples of prokaryotes include microorganisms belonging to the genus *Escherichia*, the genus *Bacillus*, the genus *Brevibacterium*, the genus *Corynebacterium*, the genus *Microbacterium*, the genus *Serratia*, the genus *Pseudomonas*, the genus *Agrobacterium*, the genus *Alicyclobacillus*, the genus *Anabena*, the genus *Anacystis*, the genus *Arthrobacter*, the genus *Azotobacter*, the genus *Chromatium*, the genus *Erwinia*, the genus *Methylobacterium*, the genus *Phormidium*, the genus *Rhodobacter*, the genus *Rhodopseudomonas*, the genus *Rhodospirillum*, the genus *Scenedesmus*, the genus *Streptomyces*, the genus *Synechoccus*, and the genus *Zymomonas*. Specific examples of such microorganisms include *Escherichia coli* XL1-Blue, *Escherichia coli* XL2-Blue® (Stratagene), *Escherichia coli* DH1, *Escherichia coli* DH5α, *Escherichia coli* MC1000, *Escherichia coli* KY3276, *Escherichia coli* W1485, *Escherichia coli* JM109, *Escheri-* chia coli HB101, *Escherichia coli* No. 49, *Escherichia coli* W3110, *Escherichia coli* NY49, *Escherichia coli* MP347, *Escherichia coli* NM522, *Escherichia coli* BL21, *Bacillus subtilis* ATCC33712, *Bacillus megaterium*, *Brevibacterium ammoniagenes*, *Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC14297, *Corynebacterium acetoacidophilum* ATCC13870, *Microbacterium ammoniaphilum* ATCC15354, *Serratia ficaria*, *Serratia fonticola*, *Serratia liquefaciens*, *Serratia marcescens*, *Pseudomonas* sp. D-0110, *Agrobacterium radiobacter*, *Agrobacterium rhizogenes*, *Agrobacterium rubi*, *Anabaena cylindrica*, *Anabaena doliolum*, *Anabaena flos-aquae*, *Arthrobacter aurescens*, *Arthrobacter citreus*, *Arthrobacter globformis*, *Arthrobacter hydrocarboglutamicus*, *Arthrobacter mysorens*, *Arthrobacter nicotianae*, *Arthrobacter paraffineus*, *Arthrobacter protophormiae*, *Arthrobacter roseoparaffinus*, *Arthrobacter sulfureus*, *Arthrobacter ureafaciens*, *Chromatium buderi*, *Chromatium tepidum*, *Chromatium vinosum*, *Chromatium warmingii*, *Chromatium fluviatile*, *Erwinia uredovora*, *Erwinia carotovora*, *Erwinia ananas*, *Erwinia herbicola*, *Erwinia punctata*, *Erwinia terreus*, *Methylobacterium rhodesianum*, *Methylobacterium extorquens*, *Phormidium* sp. ATCC29409, *Rhodobacter capsulatus*, *Rhodobacter sphaeroides*, *Rhodopseudomonas blastica*, *Rhodopseudomonas marina*, *Rhodopseudomonas palustris*, *Rhodospirillum rubrum*, *Rhodospirillum salexigens*, *Rhodospirillum salinarum*, *Streptomyces ambofaciens*, *Streptomyces aureofaciens*, *Streptomyces aureus*, *Streptomyces fungicidicus*, *Streptomyces griseochromogenes*, *Streptomyces griseus*, *Streptomyces lividans*, *Streptomyces olivogriseus*, *Streptomyces rameus*, *Streptomyces tanashiensis*, *Streptomyces vinaceus*, and *Zymomonas mobilis*.

Any method can be used as a method for introducing a recombinant DNA, as long as it is a method for introducing a DNA into the above host cells. Examples of such method include a method using calcium ions [Proc. Natl. Acad. Sci., U.S.A., 69, 2110 (1972)], a protoplast method (JP Patent Publication (Kokai) No. 63-248394 A (1988)), and electroporation [Nucleic Acids Res., 16, 6127 (1988)].

When yeast is used as a host cell, YEp13 (ATCC37115), YEp24 (ATCC37051), YCp50 (ATCC37419), pHS19, pHS15, or the like can be used as an expression vector.

Any promoter can be used as long as it functions within a yeast strain. Examples of such promoter include a PHO5 promoter, a PGK promoter, a GAP promoter, an ADH promoter, a gal 1 promoter, a gal 10 promoter, a heat shock polypeptide promoter, an MFα1 promoter, and a CUP 1 promoter.

Examples of yeast include yeast strains belonging to the genus *Saccharomyces*, the genus *Schizosaccharomyces*, the genus *Kluyveromyces*, the genus *Trichosporon*, the genus *Schwanniomyces*, the genus *Pichia*, and the genus *Candida*. Specific examples of such yeast strains include *Saccharomyces cerevisiae*, *Schizosaccharomyces pombe*, *Kluyveromyces lactis*, *Trichosporon pullulans*, *Schwanniomyces alluvius*, *Pichia pastoris*, and *Candida utilis*.

Any method for introducing a recombinant DNA can be used, as long as it is a method for introducing a DNA into yeast. Examples of such method include electroporation [Methods Enzymol., 194, 182 (1990)], the spheroplast method [Proc. Natl. Acad. Sci., U.S.A., 81, 4889 (1984)], and the lithium acetate method [J. Bacteriol., 153, 163 (1983)].

When animal cells are used as hosts, examples of expression vectors that can be used herein include pcDNAI, pcDM8 (commercially available from Funakoshi Corporation), pAGE107 (JP Patent Publication (Kokai) No. 3-22979 A (1991)), pAS3-3 (JP Patent Publication (Kokai) No. 2-227075 A (1990)), pCDM8 [Nature, 329, 840 (1987)], pcDNAI/Amp (Invitrogen Corporation), pREP4 (Invitrogen Corporation), pAGE103 [J. Biochem, 101, 1307 (1987)], pAGE210, pAMo, and pAMoA.

Any promoter can be used, as long as it functions within animal cells. Examples of such promoter include a cytomegalovirus (CMV) IE (immediate early) gene promoter or SV40 early promoter, a metallothionein promoter, a retroviral promoter, a heat shock promoter, and an SRα promoter. Moreover, a human CMV IE gene enhancer can be used together with a promoter.

Examples of animal cells include mouse myeloma cells, rat myeloma cells, mouse hybridoma cells, Namalwa cells or Namalwa KJM-1 cells that are human cells, human fetal kidney cells, human leukemia cells, African green monkey kidney cells, CHO cells that are Chinese hamster cells, and HBT5637 (JP Patent Publication (Kokai) No. 63-299 A (1988)).

Examples of mouse myeloma cells include SP2/0 and NSO. Examples of rat myeloma cells include YB2/0. Examples of human fetal kidney cells include HEK293 (ATCC CRL-1573). Examples of human leukemia cells include BALL-1. Examples of African green monkey kidney cells include COS-1 and COS-7.

Any method can be used for introducing a recombinant DNA, as long as it is a method for introducing DNA into animal cells. Examples of such method include electroporation [Cytotechnology, 3, 133 (1990)], a calcium phosphate method (JP Patent Publication (Kokai) No. 2-227075 A (1990)), lipofection [Proc. Natl. Acad. Sci., U.S.A., 84, 7413 (1987)], and a method described in Virology, 52, 456 (1973).

When insect cells are used as hosts, a protein can be produced by a method described in Baculovirus Expression Vectors, A Laboratory Manual, W. H. Freeman and Company, New York (1992), Current Protocols in Molecular Biology, Molecular Biology, A Laboratory Manual, Bio/Technology, 6, 47 (1988), or the like.

Specifically, a recombinant gene transfer vector and baculovirus are co-introduced into insect cells and then a recombinant virus is obtained in a supernatant obtained by culturing insect cells. The insect cells are further infected with the recombinant virus, so that the protein can be produced.

Examples of such gene transfer vector to be used in the method include pVL1392, pVL1393, and pBlueBacIII (all of them are manufactured by Invitrogen Corporation).

As baculovirus, *Autographa californica* nuclear polyhedrosis virus that infects insects of the genus *Mamestra* (the subfamily Hadeninae, the family Noctuidae) can be used, for example.

As insect cells, ovary cells of *Spodoptera frugiperda*, ovary cells of *Trichoplusia ni*, cultured cells derived from silkworm ovary, and the like can be used.

Examples of ovary cells of *Spodoptera frugiperda* include Sf9 and Sf21 (Baculovirus Expression Vectors: A Laboratory Manual). Examples of ovary cells of *Trichoplusia ni* include High 5 and BTI-TN-5B1-4 (Invitrogen Corporation). Examples of cultured cells derived from silkworm ovary include *Bombyx mori* N4 and the like.

Examples of a method for co-introduction of the above recombinant gene transfer vector and the above baculovirus into insect cells for preparation of a recombinant virus include a calcium phosphate method (JP Patent Publication (Kokai) No. 2-227075 A (1990)), and lipofection [Proc. Natl. Acad. Sci., U.S.A., 84, 7413 (1987)].

When plant cells are used as host cells, examples of expression vectors include a Ti plasmid and a tobacco mosaic virus vector.

Any promoter can be used, as long as it functions within plant cells. Examples of such promoter include a cauliflower mosaic virus (CaMV) 35S promoter and a rice actin 1 promoter.

Examples of host cells include plant cells of tobacco, potato, tomato, carrot, soybean, rapeseed, alfalfa, rice, wheat, barley, and the like.

Any method for introducing a recombinant vector can be used, as long as it is a method for introducing a DNA into plant cells. Examples of such method include a method using *Agrobacterium* (JP Patent Publication (Kokai) No. 59-140885 A (1984), JP Patent Publication (Kokai) No. 60-70080 A (1985), WO94/00977), electroporation (JP Patent Publication (Kokai) No. 60-251887 A (1985)), a method using a particle gun (gene gun) (JP Patent No. 2606856 and JP Patent No. 2517813).

6. Process For Producing The Protein of the Present Invention

A transformant obtained by the method in 5 above is cultured in a medium, the protein of the present invention is formed and accumulated in the culture, and then the protein is recovered from the culture. Thus, the protein can be produced.

A host for the above transformant for production of the protein of the present invention may be any of a prokaryote, yeast, an animal cell, an insect cell, a plant cell, and the like. Specific examples of such host include preferably prokaryotes such as bacteria, more preferably microorganisms belonging to the genus *Escherichia*, and further more preferably microorganisms belonging to *Escherichia coli*.

When the protein is expressed by yeast, animal cells, insect cells, or plant cells, the protein to which a sugar or a sugar chain has been added can be obtained.

The above transformant can be cultured in a medium according to a method generally employed for culturing a host.

Both a natural medium and a synthetic medium may be used as media for culturing a transformant obtained using a prokaryote such as Escherichia coli or an eukaryote such as yeast as a host, as long as it contains a carbon source, a nitrogen source, inorganic salts, and the like that can be assimilated by the relevant organisms and enables efficient culturing of the transformant.

Any carbon source can be used herein, as long as it can be assimilated by organisms. Examples of such carbon source include carbohydrates such as glucose, fructose, sucrose, molasses containing them, and starch or starch hydrolysate, organic acids such as acetic acid and propionic acid, and alcohols such as ethanol and propanol.

Examples of a nitrogen source that can be used herein include ammonia, ammonium salts of inorganic acids or organic acids such as ammonium chloride, ammonium sulfate, ammonium acetate, and ammonium phosphate, other nitrogen-containing compounds, and, peptone, a meat extract, a yeast extract, corn steep liquor, casein hydrolysate, soybean cake and soybean cake hydrolysate, various fermentation microbes, and digests thereof.

As inorganic salts, monopotassium phosphate, dipotassium phosphate, magnesium phosphate, magnesium sulfate, sodium chloride, ferrous sulfate, manganese sulfate, copper sulfate, calcium carbonate, and the like can be used.

Culturing is generally carried out under aerobic conditions by shaking culture, deep aeration stirring culture, or the like. The culturing temperature preferably ranges from 15° C. to 40° C. The culturing time generally ranges from 5 hours to 7 days. The pH during culturing is maintained between 3.0 and 11. The pH is adjusted using inorganic or organic acid, an alkaline solution, urea, calcium carbonate, ammonia, or the like.

Also, an antibiotic such as ampicillin or tetracycline may be added to a medium during culturing if necessary.

When a microorganism transformed with an expression vector containing an inducible promoter is cultured, an inducer may be added to a medium as necessary. For example, when a microorganism transformed with an expression vector containing a lac promoter is cultured, isopropyl-β-D-thiogalactopyranoside or the like may be added to the medium. When a microorganism transformed with an expression vector containing a trp promoter is cultured, indoleacrylic acid or the like may be added to the medium.

As a medium for culturing a transformant obtained using an animal cell as a host, a generally employed RPMI1640 medium [J. Am. Med. Assoc., 199, 519 (1967)], Eagle's MEM medium [Science, 122, 501 (1952)], DMEM medium [Virology, 8, 396 (1959)], or 199 medium [Proc. Soc. Biol. Med., 73, 1 (1950)] or such medium supplemented with fetal calf serum or the like can be used.

Culturing is generally carried out under conditions of pH6 to 8, 25° C. to 40° C., the presence of 5% $CO_2$, and the like for 1 to 7 days.

Also, an antibiotic such as kanamycin, penicillin, or streptomycin may be added to medium during culturing, as necessary.

As a medium for culturing a transformant obtained using an insect cell as a host, a generally employed TNM-FH medium (Pharmingen), Sf-900 II SFM medium (Life Technologies), ExCell400, ExCell405 [all of them are manufactured by JRH Biosciences], Grace's Insect Medium [Nature, 195, 788 (1962)], or the like can be used.

Culturing is generally carried out under conditions of pH6 to 7, 25° C. to 30° C., and the like for 1 to 5 days.

Also, an antibiotic such as gentamicin may be added to a medium during culturing, as necessary.

A transformant obtained using a plant cell as a host can be cultured as cells or caused to differentiate into plant cells or organs and then cultured. As a medium for culturing the transformant, a generally employed Murashige and Skoog (MS) medium, White medium, or such medium supplemented with a plant hormone such as auxin or cytokinin can be used.

Culturing is generally carried out under conditions of pH5 to 9, 20° C. to 40° C., and for 3 to 60 days.

Also, an antibiotic such as kanamycin or hygromycin may be added to a medium during culturing, as necessary.

Examples of the process for producing the protein of the present invention include a process that comprises allowing the protein produced within host cells, a process that comprises allowing the protein to be secreted outside the host cells, and a process that comprises allowing the protein to be produced on the extracellular membranes of the host cells. The structure of the protein to be produced can be varied depending on the selected method.

When the protein of the present invention is produced within host cells or on the extracellular membranes of host cells, the protein can be actively secreted by the host cells extracellularly via application of the method of Paulson et al [J. Biol. Chem., 264, 17619 (1989)], the method of Row et al [Proc. Natl. Acad. Sci., U.S.A., 86, 8227 (1989), Genes Develop., 4, 1288(1990)], or the method described in JP Patent Publication (Kokai) No. 05-336963 A (1993), WO94/23021, or the like.

Specifically, with the use of a gene recombination technique, a protein containing the active site of the protein of the present invention is produced in a form such that a signal peptide is added in front of the protein. Hence, the protein can be actively secreted outside the host cells.

Moreover, according to the method described in JP Patent Publication (Kokai) No. 2-227075 A (1990), the productivity can also be increased using a gene amplification system using a dihydrofolate reductase gene or the like.

Furthermore, gene-transferred animal or plant cells are caused to redifferentiate, so that animal individuals (transgenic non-human animals) or plant individuals (transgenic plants) into which a gene has been introduced are produced and the protein of the present invention can also be produced using these animal individuals or plant individuals.

When a transformant producing the protein of the present invention is an animal or a plant individual, such transformant is raised or cultivated according to a general method and then caused to form and accumulate the protein. The protein is recovered from the animal individual or the plant individual, so that the protein can be produced.

An example of a process for producing the protein of the present invention using an animal individual is a process by which the protein of the present invention is produced in animals that have been produced by introducing a gene according to a known method [Am. J. Clin. Nutr., 63, 639S (1996), Am. J. Clin. Nutr., 63, 627S (1996), Bio/Technology, 9, 830 (1991)].

In the case of animal individuals, the protein of the present invention can be produced by raising transgenic non-human animals in which the DNA of the present invention or a DNA to be used in the production processes of the present invention has been introduced, forming and accumulating the protein in the animals, and then recovering the protein from the animals, for example. Examples of places in which the protein is formed and accumulated in animals include the milk of animals (JP Patent Publication (Kokai) No. 63-309192 A (1988)) and eggs. Any promoter can be used in this case, as long as it functions within animals. Examples of such promoter that is preferably used include mammary-cell-specific promoters such as an α casein promoter, a β casein promoter, a β lactoglobulin promoter, and a whey acid protein promoter.

An example of a process for producing the protein of the present invention using a plant individual is a process that involves cultivating a transgenic plant (into which a DNA encoding the protein of the present invention has been introduced) according to a known method [Tissue Culture, 20 (1994), Tissue Culture, 21 (1995), Trends Biotechnol., 15, 45 (1997)], forming and accumulating the protein in the plant, and then recovering the protein from the plant, so as to produce the protein.

As a method for isolating and purifying the protein of the present invention produced using a transformant that produces the protein of the present invention, a general isolation and purification method for enzymes can be employed.

For example, when the protein of the present invention is produced in a soluble state within the cells, after completion of culturing, the cells are collected by centrifugation, suspended in a water-based buffer, and then disrupted using a ultrasonic disintegrator, French press, Manton-Gaulin homogenizer, dyno mill, or the like, thereby obtaining a cell-free extract.

Purified proteins can be obtained from supernatants obtained by centrifugation of the cell-free extracts using one of or a combination of general enzyme isolation and purification techniques, that is, solvent extraction, a salting-out method using ammonium sulfate or the like, demineralization, precipitation using an organic solvent, anion exchange chromatography using a resin such as diethylaminoethyl (DEAE)-Sepharose® (crosslinked beaded form of agarose, GE Healthcare) or DIAION® HPA-75 (macroporous styrene-divinylbenzene copolymer ion-exchange resin, Mitsubishi Chemical Corporation), cation exchange chromatography using a resin such as S-Sepharose® FF (Pharmacia), hydrophobic chromatography using a resin such as butyl Sepharose® or phenyl Sepharose®, gel filtration using a molecular sieve, affinity chromatography, electrophoresis such as chromatofocusing and isoelectric focusing, and the like.

Furthermore, when the protein is produced in an insoluble form formed within cells, cells are collected and disrupted similarly, and then centrifuged to obtain a precipitated fraction. The protein is then recovered from the fraction by a general method and then the insoluble form of the protein is solubilized using a protein denaturation agent.

The solution obtained by solubilization is diluted to prepare a dilute solution such that it contains no protein denaturation agent or the concentration of the protein denaturation agent is low enough so that the protein is not denatured. Alternatively the solution is dialyzed. Thus, the protein is formed to have a normal conformation, and then a purified protein can be obtained by isolation and purification techniques similar to the above.

When the protein of the present invention or a derivative such as a sugar-modified product thereof is secreted extracellularly, the protein or a derivative such as a glycosylated product thereof can be recovered in the supernatant of the culture.

Specifically, the culture is treated by a technique similar to the above such as centrifugation, so as to obtain a soluble fraction. A purified protein can be obtained from the soluble fraction using isolation and purification techniques similar to the above.

An example of the thus obtained protein is a protein having the amino acid sequence shown by SEQ ID NO: 1.

Also, the protein of the present invention is produced in the form of a fusion protein with another protein and then the protein can also be purified by affinity chromatography using a substance that has affinity for the protein of interest fused to the other protein. For example, according to the method of Row et al [Proc. Natl. Acad. Sci., U.S.A., 86, 8227 (1989), Genes Develop., 4, 1288 (1990)] or the method described in JP Patent Publication (Kokai) No. 5-336963 A (1993) or WO94/23021, the protein of the present invention is produced as a fusion protein with protein A and then the protein of interest can be purified by affinity chromatography using immunoglobulin G.

Furthermore, the protein of the present invention is produced as a fusion protein with a Flag peptide and then the protein can also be purified by affinity chromatography using an anti-Flag antibody [Proc. Natl. Acad. Sci., U.S.A., 86, 8227 (1989), Genes Develop., 4, 1288 (1990)]. Alternatively, the protein is produced as a fusion protein with polyhistidine and then can be purified by affinity chromatography using a metal coordination resin having high affinity for polyhistidine. Moreover, the protein can also be purified by affinity chromatography using an antibody against the protein itself.

Based on the amino acid sequence information of the above-obtained protein, the protein of the present invention can be produced by a chemical synthesis method such as a Fmoc method (fluorenylmethyloxycarbonyl method), a tBoc method (t-butyloxycarbonyl method), or the like. Also, the protein can also be chemically synthesized using a peptide synthesizer of Advanced ChemTech, Perkin Elmer Co., Ltd., Pharmacia, Protein Technology Instrument, Synthecell-Vega, Applied Biosystems, Shimadzu Corporation, or the like.

7. Process For Producing A Dipeptide of the Present Invention

The culture or the treated culture of a microorganism or a transformant in 3 above, or the protein of the present invention in 1 above and one or more kinds of amino acid are allowed to be present in an aqueous medium. A dipeptide is formed and accumulated in the medium, and then the dipeptide is recovered from the medium, so that the dipeptide can be produced.

(1) Process for Producing a Dipeptide Using the Protein of the Present Invention as an Enzyme Source When the protein of the present invention is used as an enzyme source in the process of the present invention, any combinations of any amino acids may be used as one or two kinds of amino acid to be used as a substrate, as long as they are selected from the group consisting of L-amino acid, Gly, and β-alanine ((β-Ala). Examples of L-amino acid include one or two kinds of amino acid selected from among L-Ala, L-Gln, L-Glu, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, Gly, and β-Ala.

Examples of amino acids to be used in the above process include: preferably a combination of one kind of amino acid selected from among L-Arg, L-Lys, and L-His and an amino acid selected from the group consisting of L-amino acid, Gly, and β-Ala and more preferably a combination of L-Arg with L-Ala, L-Gln, L-Glu, L-Val, L-Leu, L-Ile, L-Pro, L-Phe, L-Trp, L-Met, L-Ser, L-Thr, L-Cys, L-Asn, L-Lys, L-Arg, L-His, L-Asp, and Gly; and a combination of L-Lys alone and particularly preferably a combination of L-Arg with one kind of amino acid selected from among L-Ala, L-Arg, L-Ser, L-His, L-Asn, and Gly.

In the above process, 0.01 mg to 100 mg and preferably 0.1 mg to 10 mg of the protein of the present invention is added per mg of amino acid to be used as a substrate.

In the above process, amino acid to be used as a substrate is added initially or during the reaction to an aqueous medium at a concentration ranging from 0.1 g/L to 500 g/L and preferably ranging from 0.2 g/L to 200 g/L.

In the above process, ATP can be used as an energy source at a concentration ranging from 0.5 mmol to 10 mol/L.

An aqueous medium to be used in the above process may have any ingredients or composition, as long as a reaction for dipeptide production is not inhibited. Examples of such aqueous medium include water, a phosphate buffer, a carbonate buffer, an acetate buffer, a borate buffer, a citrate buffer, and a tris buffer. Also, such an aqueous medium may contain alcohols such as methanol and ethanol, esters such as ethyl acetate, ketones such as acetone, and amides such as acetamide.

The reaction for dipeptide production is carried out in an aqueous medium under conditions of pH 5 to 11 and preferably pH 6 to 10, and 20° C. to 50° C. and preferably 25° C. to 45° C. for 2 to 150 hours and preferably 6 to 120 hours.

Examples of a dipeptide to be produced by the above process include: a dipeptide in which one or two kinds of amino acid selected from among L-Ala, L-Gln, L-Glu, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, Gly, and β-Ala are linked via peptide bonds; preferably a dipeptide in which one kind of amino acid selected from among L-Arg, L-Lys, and L-His and one kind of amino acid selected from the group consisting of L-amino acid, Gly, and β-Ala are linked via peptide bonds; more preferably a dipeptide in which L-Arg and one kind of amino acid selected from among L-Ala, L-Gln, L-Glu, L-Val, L-Leu, L-Ile, L-Pro, L-Phe, L-Trp, L-Met, L-Ser, L-Thr, L-Cys, L-Asn, L-Lys, L-Arg, L-His, L-Asp, and Gly are linked via peptide bonds; and a dipeptide containing L-Lys-L-Lys, more preferably a dipeptide in which L-Arg and one kind of amino acid selected from among L-Ala, L-Arg, L-Ser, L-His, L-Asn, and Gly are linked via peptide bonds, and most preferably a dipeptide in which two amino acids are linked via peptide bonds, which dipeptide is represented by formula (I)

(where, $R^1$ is L-Arg, $R^2$ is one kind of amino acid selected from among L-Ala, L-Arg, L-Ser, and L-His).

(2) Process for Producing a Dipeptide Using the Culture or the Treated Culture of a Microorganism or a Transformant as an Enzyme Source An example of the culture of a microorganism or a transformant, which is used as an enzyme source in the process of the present invention is a culture that is obtained by culturing the microorganism or the transformant by the culturing method in 6 above. Examples of the treated culture of a microorganism or a transformant include those containing living cells retaining functions, as enzyme sources, similar to those of the culture, such as a concentrated culture, a dried culture, cell obtained by centrifugation, filtration, or the like of the culture, a dried cell, a freeze-dried cell, a cell treated with a surfactant, a cell treated with a solvent, a cell treated with an enzyme, and an immobilized cell.

When the culture or the treated culture of a transformant or a microorganism is used as an enzyme source, an example of one or more kinds of amino acid to be used as a substrate is an amino acid(s) similar to that (those) in (1) above.

The amount of the enzyme source differs depending on the specific activity or the like of the enzyme source. For example, 5 mg to 1000 mg and preferably 10 mg to 400 mg as wet microbial weight (weight of wet microbial mass) of the enzyme source is added per mg of amino acid to be used as a substrate.

Amino acid to be used as a substrate can be added into an aqueous medium in a manner similar to that in (1) above. ATP is allowed to be present in an aqueous medium in a manner similar to that in (1) above, so that ATP can be used as an energy source.

Media in (1) above can be used as aqueous media. In addition, a supernatant of the culture of a microorganism or a transformant, which is used as an enzyme source, can also be used as an aqueous medium.

Also in the above process, a surfactant or an organic solvent may also be added into an aqueous medium, as necessary. Any surfactant may be used herein, as long as it accelerates the production of dipeptide. Examples of such surfactant include nonionic surfactants such as polyoxyethylene octadecylamine (e.g., NYMEEN S-215, NOF Corporation), cationic surfactants such as cetyltrimethylammonium bromide and alkyldimethylbenzylammonium chloride (e.g., cation F2-40E, NOF Corporation), anionic surfactants such as lauroyl sarcosinate, and tertiary amines such as alkyldimethylamine (e.g., tertiary amine FB, NOF Corporation). One kind or several kinds thereof can also be mixed and then used. Such a surfactant is generally used at a concentration ranging from 0.1 g/l to 50 g/l. Examples of an organic solvent include xylene, toluene, aliphatic alcohol, acetone, and ethyl acetate and such an organic solvent is generally used at a concentration ranging from 0.1 ml/l to 50 ml/l.

The reaction conditions for a reaction for dipeptide production are the same conditions as those in (1) above, for example.

An example of a dipeptide to be produced by the above process is the same dipeptide as that in (1) above.

In the processes in (1) and (2) above, a dipeptide that is formed and accumulated in an aqueous medium can be recovered by a general method using activated carbon, an ion exchange resin, or the like, or extraction using an organic solvent, crystallization, thin-layer chromatography, high-performance liquid chromatography, or the like.

Hereafter, the present invention is described in detail with reference to Examples, although the present invention is not limited thereto.

Example 1

Construction of a Strain Expressing a Rhizocticin Synthetase Gene

A rhizocticin synthetase gene encoding a protein with unknown functions was obtained as follows, having the nucleotide sequence shown by SEQ ID NO: 2 existing on the chromosomal DNA of *Bacillus subtilis* ATCC6633.

First, *Bacillus subtilis* ATCC6633 was spread on an YPGA medium [7 g/L yeast extract (Difco), 7 g/L bacto peptone (Difco), 7 g/L glucose, and 1.5 g/L agar] and statically cultured at 30° C. overnight. One platinum loop of the thus grown cells was inoculated in 3 mL of YPG medium [7 g/L yeast extract (Difco), 7 g/L bacto peptone (Difco), and 7 g/L glucose], followed by 24 hours of shaking culture at 30° C. Chromosomal DNA was prepared using a Dneasy® Kit (QIAGEN) from cells collected by centrifugation.

DNAs having the nucleotide sequences shown by SEQ ID NOS: 3 and 4 (hereinafter, referred to as primer A and primer B, respectively) were synthesized using a Model 8905 DNA Synthesizer (Perseptive Biosystems).

For amplification of a rhizocticin synthetase gene fragment, PCR was carried out using the above primer A and primer B and the chromosomal DNA of *Bacillus subtilis* ATCC6633 as a template. PCR was carried out as follows. 50 µL of a reaction solution containing 0.50 pg of total DNA, the primers (0.3 µmol/L each), 1 unit of KOD plus DNA polymerase (Toyobo Co., Ltd.), 5 µL of ×10 buffer for KOD plus DNA polymerase (Toyobo Co., Ltd.), and dNTP (200 µmol/L each) (dATP, dGTP, dCTP, and dTTP) was prepared. After heating at 94° C. for 120 seconds, a step of 94° C. for 15 seconds, 50° C. for 30 seconds, and 68° C. for 120 seconds was repeated 25 times, followed by 5 minutes of heating at 68° C. 1/10 the amount of the reaction solution was subjected to agarose gel electrophoresis, so that the amplification by PCR of an approximately 1.2-kb DNA fragment corresponding to the rhizocticin synthetase gene was confirmed.

Next, 20 µL of a reaction solution containing 1.46 µL of the remaining reaction solution, 2.5 mM dGTP, 5 mM dithiothreitol (DTT), 1 unit of T4 DNA polymerase, and 2 µL of ×10 buffer for T4 DNA polymerase (Novagen) was prepared. After 30 minutes of reaction at 22° C., the reaction was stopped by heating at 75° C. for 20 minutes.

2 µL of the reaction solution was mixed with 1 µL of LIV vector pET-30 Xa/LIC (Novagen). After 5 minutes of reaction at 22° C., 1 µL of 25 mM EDTA was added to the mixture and then a reaction was further carried out at 22° C.

*Escherichia coli* strain JM109 was transformed by a heat shock method using the reaction solution. The transformant was applied on LB agar medium containing 25 µg/mL kanamycin and was incubated at 30° C. overnight, so that a transformed cell was selected.

The transformed cell was cultured overnight in LB medium containing 20 µg/ml kanamycin. A plasmid was prepared by an alkaline SDS method (Molecular Cloning, $3^{rd}$ Edition) from the thus obtained culture solution.

Restriction enzyme digestion analysis was carried out. It was confirmed that the plasmid had a structure in which an approximately 1.2-kb DNA fragment (obtained above) had been inserted into pET-30 Xa/LIC. This plasmid was designated pBsRzcA.

*Escherichia coli* strain Rosetta (DE3) (Novagen) was transformed with pBsRzcA by a method using calcium ions. The transformant was applied on LB agar medium containing 25 µg/mL kanamycin and 25 µg/mL chloramphenicol and then the transformant was cultured overnight at 30° C., so that a transformed cell was selected.

A plasmid was extracted according to a known method from colonies of the transformant that had grown. The structure was analyzed using a restriction enzyme, so as to confirm that pBsRzcA was obtained.

The transformed cell was designated *Escherichia coli* Rosetta (DE3)/pBsRzcA.

Example 2

Production of A Protein Having Dipeptide-Synthesizing Activity

*Escherichia coli* Rosetta (DE3)/pBsRzcA obtained in Example 1 was inoculated in a test tube containing 3 mL of LB medium containing 25 µg/mL kanamycin and 25 µg/mL chloramphenicol, followed by 12 hours of shaking culture at 37° C. 1 mL of the thus obtained culture solution was introduced into a 500-mL Erlenmeyer flask containing 100 mL of LB medium containing 25 µg/mL kanamycin and 25 µg/mL chloramphenicol. After 3 hours of shaking culture at 25° C., isopropyl-β-D-thiogalactopyranoside (IPTG) with a final concentration of 1 mmol/L was added and then shaking culture was further carried out at 25° C. for 12 hours. The culture was centrifuged, so that wet cells were obtained.

The wet cells were disrupted by ultrasonication and then the resultant was subjected to centrifugation. From the thus obtained supernatant, an His-tagged protein was purified using HisTrap® (His-tagged protein purification kit, Amersham).

Example 3

Production of a Dipeptide Using an His-Tagged Protein

A reaction solution was prepared containing the purified His-tagged protein (0.1 mg/mL) obtained in Example 2, 50 mmol/L Tris-HCl buffer (pH 8.0), 12.5 mmol/L magnesium sulfate, 12.5 mmol/L ATP, 12 5 mmol/L L-arginine, and one kind of L-amino acid (12.5 mmol/L) (selected from among L-alanine (L-Ala), L-glutamine (L-Gln), L-glutamic acid (L-Glu), L-valine (L-Val), L-leucine (L-Leu), L-isoleucine (L-Ile), L-proline (L-Pro), L-phenylalanine (L-Phe), L-tryptophan (L-Trp), L-methionine (L-Met), L-serine (L-Ser), L-threonine (L-Thr), L-cysteine (L-Cys), L-asparagine (L-Asn), L-lysine (L-Lys), L-arginine (L-Arg), L-histidine (L-His), and L-aspartic acid (L-Asp)) or glycine (Gly). Reaction was carried out at 30° C. for 17 hours. Furthermore, a reaction solution was prepared, containing the purified His-tagged protein (0.1 mg/mL) obtained in Example 2, 50 mmol/L Tris-HCl buffer (pH 8.0), 12.5 mmol/L magnesium sulfate, 12.5 mmol/L ATP, and 25 mmol/L L-lysine. Reaction was carried out at 30° C. for 17 hours. After completion of the reaction, the thus formed products were identified by three types of technique including determination of the amounts of phosphoric acid that had been liberated in the reaction solutions using a Determiner L IP (Kyowa Medex Co., Ltd.), MALDI-TOFMS (Matrix Assisted Laser Desorption/Ionization—Time of Flight Mass Spectrometry) analysis, and NMR (Nuclear Magnetic Resonance) analysis.

As a result of determination of the amounts of liberated phosphoric acid, the production of a dipeptide was confirmed, in which L-Arg was bound to an L-amino acid selected from among L-Ala, L-Gln, L-Glu, L-Val, L-Leu, L-Ile, L-Pro, L-Phe, L-Trp, L-Met, L-Ser, L-Thr, L-Cys, L-Asn, L-Lys, L-His, and L-Asp or bound to Gly; and the production of Arg-Arg and Lys-Lys was confirmed. As a result of MALDI-TOFMS analysis, the production of a dipeptide was confirmed, in which L-Arg was bound to an L-amino acid selected from among L-Ala, L-Ser, and L-Asn or bound to Gly. Moreover, NMR analysis of the structures of the products and the amounts of the products revealed that Arg-Ala was produced at 0.89 mmol/L, Arg-Arg was produced at 1.65 mmol/L, Arg-Ser was produced at 3.1 mmol/L, and Arg-His was produced at 1.9 mmol/L.

As described above, it was revealed that the protein of the present invention has activity of linking one or two kinds of amino acid via peptide bonds, so as to produce various dipeptides.

INDUSTRIAL APPLICABILITY

According to the present invention, a protein having dipeptide-synthesizing activity can be produced. Moreover, a dipeptide can be produced using the protein, or a transformant or a microorganism capable of producing the protein.

Sequence Listing Free Text

SEQ ID NO: 3-explanation of artificial sequence: synthetic DNA

SEQ ID NO: 4-explanation of artificial sequence: synthetic DNA

The invention claimed is:

1. A purified DNA selected from the group consisting of:
 (A) a DNA encoding a protein having the amino acid sequence of SEQ ID NO:1;
 (B) a DNA having the nucleotide sequence of SEQ ID NO: 2; and
 (C) a DNA hybridizing under stringent conditions to a DNA consisting of a full complement of the nucleotide sequence of SEQ ID NO: 2 and encoding a protein having dipeptide-synthesizing activity, wherein said stringent conditions comprise incubation in a solution containing 50% formamide and 5×SSC at 42° C. followed by washing in 0.2×SSC at 65° C.

2. A recombinant DNA containing the DNA of claim 1.

3. An isolated transformant transformed with the recombinant DNA of claim 2.

4. The transformant of claim 3, wherein the transformant is obtained from a bacterial host.

5. The transformant of claim 4, wherein the bacterial host is *Escherichia*.

6. A process for producing a protein, comprising:
 culturing the transformant of claim 3 in a medium to produce the protein;
 accumulating the protein in a culture; and
 recovering the protein from the culture, wherein the protein is encoded by the DNA of (A), (B) or (C).

7. A process for producing a dipeptide comprising:
 contacting a culture or a treated culture of the transformant of claim 3 with amino acids in an aqueous medium;
 forming and accumulating the dipeptide in the medium; and
 recovering the dipeptide from the medium.

8. The process of claim 6, wherein the transformant is obtained from a bacterial host.

9. The process of claim 8, wherein the bacterial host is *Escherichia*.

10. The process of claim 7, wherein the transformant is obtained from a bacterial host.

11. The process of claim 10, wherein the bacterial host is *Escherichia*.

* * * * *

SEQUENCE LISTING

```
<160> NUMBER OF SEQ ID NOS: 4

<210> SEQ ID NO 1
<211> LENGTH: 413
<212> TYPE: PRT
<213> ORGANISM: Bacillus subtilis

<400> SEQUENCE: 1

Met Leu Arg Ile Leu Leu Ile Asn Ser Asp Lys Pro Glu Pro Ile Gln
1               5                   10                  15

Phe Phe Gln Lys Asp Lys Glu Thr Asn Asp Ser Ile Asn Ile Ser Val
                20                  25                  30

Ile Thr Arg Ser Cys Tyr Ala Pro Leu Tyr Ser His Trp Ala Asp His
            35                  40                  45

Val Tyr Ile Val Asp Asp Val Thr Asp Leu Thr Val Met Lys Ser Leu
        50                  55                  60

Met Leu Glu Ile Leu Lys Val Gly Pro Phe Asp His Ile Val Ser Thr
65                  70                  75                  80

Thr Glu Lys Ser Ile Leu Thr Gly Gly Phe Leu Arg Ser Tyr Phe Gly
                85                  90                  95

Ile Ala Gly Pro Gly Phe Glu Thr Ala Leu Tyr Met Thr Asn Lys Leu
            100                 105                 110

Ala Met Lys Thr Lys Leu Lys Met Glu Gly Ile Pro Val Ala Asp Phe
        115                 120                 125

Leu Cys Val Ser Gln Val Glu Asp Ile Pro Ala Ala Gly Glu Lys Leu
    130                 135                 140

Gly Trp Pro Ile Ile Val Lys Pro Ala Leu Gly Ser Gly Ala Leu Asn
145                 150                 155                 160

Thr Phe Ile Ile His Ser Leu Asp His Tyr Glu Asp Leu Tyr Ser Thr
                165                 170                 175

Ser Gly Gly Leu Gly Glu Leu Lys Lys Asn Asn Ser Leu Met Ile Ala
            180                 185                 190
```

```
        Glu Lys Cys Ile Glu Met Glu Glu Phe His Cys Asp Thr Leu Tyr Ala
                    195                 200                 205

Asp Gly Glu Ile Leu Phe Val Ser Ile Ser Lys Tyr Thr Val Pro Leu
            210                 215                 220

Leu Lys Gly Met Ala Lys Ile Gln Gly Ser Phe Ile Leu Ser Gln Asn
        225                 230                 235                 240

Asp Pro Val Tyr Ala Glu Ile Leu Glu Leu Gln Lys Ser Val Ala Gln
                        245                 250                 255

Ala Phe Arg Ile Thr Asp Gly Pro Gly His Leu Glu Ile Tyr Arg Thr
                    260                 265                 270

His Ser Gly Glu Leu Ile Val Gly Glu Ile Ala Met Arg Ile Gly Gly
                275                 280                 285

Gly Gly Ile Ser Arg Met Ile Glu Lys Lys Phe Asn Ile Ser Leu Trp
            290                 295                 300

Glu Ser Ser Leu Asn Ile Ser Val Tyr Arg Asp Pro Asn Leu Thr Val
        305                 310                 315                 320

Asn Pro Ile Glu Gly Thr Val Gly Tyr Phe Ser Leu Pro Cys Arg Asn
                        325                 330                 335

Gly Thr Ile Lys Glu Phe Thr Pro Ile Glu Glu Trp Glu Lys Leu Ala
                    340                 345                 350

Gly Ile Leu Glu Val Glu Leu Leu Tyr Gln Glu Gly Asp Val Val Asp
                355                 360                 365

Glu Lys Gln Ser Ser Ser Phe Asp Leu Ala Arg Leu Tyr Phe Cys Leu
            370                 375                 380

Glu Asn Glu Asn Glu Val Gln His Leu Leu Ala Leu Val Lys Gln Thr
        385                 390                 395                 400

Tyr Tyr Leu His Leu Thr Glu Asp His Met Met Asn Gln
                        405                 410

<210> SEQ ID NO 2
<211> LENGTH: 1242
<212> TYPE: DNA
<213> ORGANISM: Bacillus subtilis
<220> FEATURE:
<221> NAME/KEY: CDS
<222> LOCATION: (1)..(1242)

<400> SEQUENCE: 2 atg ctt cgt att tta ctc att aat tcc gat aaa cca gag cct att cag      48
Met Leu Arg Ile Leu Leu Ile Asn Ser Asp Lys Pro Glu Pro Ile Gln
1               5                   10                  15 ttt ttt caa aaa gat aag gaa aca aat gat tct atc aat ata tct gtc      96
Phe Phe Gln Lys Asp Lys Glu Thr Asn Asp Ser Ile Asn Ile Ser Val
                20                  25                  30 att acg aga tcg tgc tat gcc cct ctt tat tca cat tgg gca gat cat     144
Ile Thr Arg Ser Cys Tyr Ala Pro Leu Tyr Ser His Trp Ala Asp His
            35                  40                  45 gta tac atc gtt gat gat gta aca gat tta acg gtg atg aag agt ttg     192
Val Tyr Ile Val Asp Asp Val Thr Asp Leu Thr Val Met Lys Ser Leu
    50                  55                  60 atg ctg gag ata tta aaa gtg ggg cca ttt gat cat att gtt tca aca     240
Met Leu Glu Ile Leu Lys Val Gly Pro Phe Asp His Ile Val Ser Thr
65                  70                  75                  80 acc gaa aag agt ata tta aca ggc ggg ttt ctt cgc tcc tat ttt ggg     288
Thr Glu Lys Ser Ile Leu Thr Gly Gly Phe Leu Arg Ser Tyr Phe Gly
                85                  90                  95 ata gcc ggg cct gga ttt gaa aca gct ctt tat atg acg aat aaa ttg     336
Ile Ala Gly Pro Gly Phe Glu Thr Ala Leu Tyr Met Thr Asn Lys Leu
            100                 105                 110
```

| | | | | | | | | | | | | | | | |
|---|---|---|---|---|---|---|---|---|---|---|---|---|---|---|---|
| gca | atg | aag | act | aaa | ctt | aaa | atg | gaa | ggg | att | cct | gtt | gca | gat | ttt |
| Ala | Met | Lys | Thr | Lys | Leu | Lys | Met | Glu | Gly | Ile | Pro | Val | Ala | Asp | Phe |
| | | 115 | | | | | 120 | | | | | 125 | | | |

```
gca atg aag act aaa ctt aaa atg gaa ggg att cct gtt gca gat ttt      384
Ala Met Lys Thr Lys Leu Lys Met Glu Gly Ile Pro Val Ala Asp Phe
        115                 120                 125 ttg tgt gta agc caa gta gag gat atc cct gca gca ggc gag aaa cta      432
Leu Cys Val Ser Gln Val Glu Asp Ile Pro Ala Ala Gly Glu Lys Leu
130                 135                 140 ggc tgg cct att att gta aag ccg gct ctt ggt tcg ggc gcc tta aat      480
Gly Trp Pro Ile Ile Val Lys Pro Ala Leu Gly Ser Gly Ala Leu Asn
145                 150                 155                 160 act ttt atc atc cat tca tta gat cat tac gaa gac ctg tat tca aca      528
Thr Phe Ile Ile His Ser Leu Asp His Tyr Glu Asp Leu Tyr Ser Thr
                165                 170                 175 tcg ggt ggt tta ggc gaa cta aag aag aat aac tca ctt atg att gct      576
Ser Gly Gly Leu Gly Glu Leu Lys Lys Asn Asn Ser Leu Met Ile Ala
        180                 185                 190 gaa aaa tgt ata gaa atg gaa gag ttt cat tgt gat act tta tac gct      624
Glu Lys Cys Ile Glu Met Glu Glu Phe His Cys Asp Thr Leu Tyr Ala
    195                 200                 205 gac gga gaa att ctt ttt gta tca ata tca aaa tat aca gtg cct ttg      672
Asp Gly Glu Ile Leu Phe Val Ser Ile Ser Lys Tyr Thr Val Pro Leu
210                 215                 220 cta aaa gga atg gct aaa atc caa ggg tca ttt att ttg agt caa aat      720
Leu Lys Gly Met Ala Lys Ile Gln Gly Ser Phe Ile Leu Ser Gln Asn
225                 230                 235                 240 gat ccg gtt tat gct gaa ata tta gaa ctt cag aag tct gtt gct caa      768
Asp Pro Val Tyr Ala Glu Ile Leu Glu Leu Gln Lys Ser Val Ala Gln
                245                 250                 255 gcg ttt cgt atc aca gac ggt ccc ggg cat ctt gaa ata tac aga acc      816
Ala Phe Arg Ile Thr Asp Gly Pro Gly His Leu Glu Ile Tyr Arg Thr
        260                 265                 270 cat tca ggt gaa ctg atc gtc ggt gag att gca atg cgt att ggg ggc      864
His Ser Gly Glu Leu Ile Val Gly Glu Ile Ala Met Arg Ile Gly Gly
    275                 280                 285 gga ggg atc agc cgc atg ata gaa aaa aaa ttc aat ata tct tta tgg      912
Gly Gly Ile Ser Arg Met Ile Glu Lys Lys Phe Asn Ile Ser Leu Trp
290                 295                 300 gaa agt tct ctt aac att tcc gta tat aga gat cca aat ctc acg gtc      960
Glu Ser Ser Leu Asn Ile Ser Val Tyr Arg Asp Pro Asn Leu Thr Val
305                 310                 315                 320 aat cca ata gag gga act gtc gga tac ttt agc ttg cct tgc cga aac     1008
Asn Pro Ile Glu Gly Thr Val Gly Tyr Phe Ser Leu Pro Cys Arg Asn
                325                 330                 335 gga aca ata aaa gaa ttt acg ccc atc gag gaa tgg gaa aag ctt gct     1056
Gly Thr Ile Lys Glu Phe Thr Pro Ile Glu Glu Trp Glu Lys Leu Ala
        340                 345                 350 ggc ata ctg gag gtt gaa ttg tta tac caa gaa ggt gat gtt gta gat     1104
Gly Ile Leu Glu Val Glu Leu Leu Tyr Gln Glu Gly Asp Val Val Asp
    355                 360                 365 gaa aag caa agt tca agt ttt gat ctg gcc agg ctt tat ttt tgt tta     1152
Glu Lys Gln Ser Ser Ser Phe Asp Leu Ala Arg Leu Tyr Phe Cys Leu
370                 375                 380 gaa aat gag aat gaa gta caa cat cta tta gct cta gtc aaa caa aca     1200
Glu Asn Glu Asn Glu Val Gln His Leu Leu Ala Leu Val Lys Gln Thr
385                 390                 395                 400 tat tat ctt cac tta aca gag gat cat atg atg aac caa taa             1242
Tyr Tyr Leu His Leu Thr Glu Asp His Met Met Asn Gln
                405                 410

<210> SEQ ID NO 3
<211> LENGTH: 30
```

```
<212> TYPE: DNA
<213> ORGANISM: Artificial Sequence
<220> FEATURE:
<223> OTHER INFORMATION: Synthetic DNA

<400> SEQUENCE: 3
ggtattgagg gtcgcatgct tcgtatttta                                      30

<210> SEQ ID NO 4
<211> LENGTH: 32
<212> TYPE: DNA
<213> ORGANISM: Artificial Sequence
<220> FEATURE:
<223> OTHER INFORMATION: Synthetic DNA

<400> SEQUENCE: 4
agaggagagt tagagcctta ttggttcatc at                                   32
```